US012618817B2

(12) United States Patent
Hung et al.

(10) Patent No.: US 12,618,817 B2
(45) Date of Patent: May 5, 2026

(54) COMPACT DEHYDRATION AND TRAP MODULE

(71) Applicant: Thermo Fisher (Shanghai) Instrument Co., Ltd., Shanghai (CN)

(72) Inventors: Te Yu Hung, Shanghai (CN); Chien Kuo Chang, Shanghai (CN); Colin Zou, Shanghai (CN); Rong Hua Chen, Shanghai (CN); Jun Fang, Shanghai (CN)

(73) Assignee: Thermo Fisher Scientific (Shanghai) Instruments Co., Ltd., Shanghai (CN)

( * ) Notice: Subject to any disclaimer, the term of this patent is extended or adjusted under 35 U.S.C. 154(b) by 452 days.

(21) Appl. No.: 18/472,963

(22) Filed: Sep. 22, 2023

(65) Prior Publication Data

US 2024/0102980 A1 Mar. 28, 2024

(30) Foreign Application Priority Data

Sep. 27, 2022 (CN) .......................... 202211178331.5

(51) Int. Cl.
*G01N 1/40* (2006.01)
*G01N 33/00* (2006.01)
(52) U.S. Cl.
CPC ..... *G01N 33/0016* (2013.01); *G01N 33/0026* (2013.01)
(58) Field of Classification Search
None
See application file for complete search history.

(56) References Cited

U.S. PATENT DOCUMENTS 5,847,291 A 12/1998 Green et al.
2010/0107730 A1* 5/2010 Aono ..................... G01N 30/16
73/23.39

(Continued)

FOREIGN PATENT DOCUMENTS

CN 103123308 A 5/2013
CN 105865853 A 8/2016

(Continued)

OTHER PUBLICATIONS

Extended European Search Report from EP 23198502.9, dated Jan. 25, 2024, 11 pages.

*Primary Examiner* — John E Breene
*Assistant Examiner* — Alex T Devito
(74) *Attorney, Agent, or Firm* — Klarquist Sparkman, LLP

(57) ABSTRACT

Gas detection devices comprise a dehydration unit a concentration unit, and a temperature control unit for controlling a temperature. The gas detection device includes a sampling mode in which sample gas flows into and out of the dehydration unit through a first port and a second port, respectively, wherein the volatile organic compounds in the sample gas are concentrated in the concentration unit. The temperature control unit may be configured such that the temperature of the sample gas after flowing out from the dehydration unit and before flowing into the concentration unit is not greater than a first preset temperature. Generation of condensed substances in the sample gas can be effectively avoided in a simple manner after the sample gas flows into the concentration unit, thereby further preventing ice blockage. Methods for detecting volatile organic compounds in a sample gas are also disclosed.

11 Claims, 3 Drawing Sheets

100

(56)                    References Cited

U.S. PATENT DOCUMENTS

| | | | |
|---|---|---|---|
| 2011/0023581 A1 | 2/2011 | Chou et al. | |
| 2014/0080221 A1 | 3/2014 | Stollings | |
| 2015/0289782 A1 | 10/2015 | Peverall et al. | |
| 2019/0118171 A1 * | 4/2019 | Cardin | G01N 30/461 |
| 2019/0137458 A1 | 5/2019 | Cardin | |
| 2022/0266192 A1 | 8/2022 | Heo et al. | |

FOREIGN PATENT DOCUMENTS

| | | | |
|---|---|---|---|
| CN | 111060386 A | 4/2020 | |
| CN | 210720282 U | 6/2020 | |
| CN | 111521454 A | 8/2020 | |
| CN | 211453104 U | 9/2020 | |
| CN | 112839727 A | 5/2021 | |
| CN | 214276306 U | 9/2021 | |
| JP | 2000292320 A | 10/2000 | |
| JP | 2000318695 A | 11/2000 | |
| JP | 2017020738 A | 1/2017 | |
| KR | 100355595 B1 * | 10/2002 | |
| KR | 20090061864 A | 6/2009 | |

* cited by examiner

COMPACT DEHYDRATION AND TRAP MODULE

CROSS REFERENCE TO RELATED APPLICATIONS

This application claims priority from China Application No. 202211178331.5, filed on Sep. 27, 2022, which is incorporated herein by reference in its entirety.

TECHNICAL FIELD

The present invention relates to a gas detection device for detecting volatile organic compounds (VOCs) in a sample gas. The present invention further relates to a method for detecting volatile organic compounds in a sample gas by using a gas detection device.

BACKGROUND ART

Currently, volatile organic compounds (VOCs) in the ambient atmosphere, especially in the lower troposphere, has attracted increasing and extensive attention. Definitions of volatile organic compounds are not completely consistent among different organizations around the world. For example, the World Health Organization (WHO) defines a large class of organic compounds whose boiling point ranges from 50° C. to 260° C., whose saturated vapor pressure exceeds 13.33 Pa at room temperature, and which exist in the air in the form of vapor at room temperature as volatile organic compounds. As another example, the U.S. Environmental Protection Agency defines any carbon compound that participates in atmospheric photochemical reactions except carbon monoxide, carbon dioxide, carbonic acid, metal carbide, metal carbonate and ammonium carbonate as volatile organic compounds. The American Society for Testing and Materials directly defines any organic compound that can participate in atmospheric chemical reactions as volatile organic compounds. Overall, volatile organic compounds mainly include alkanes, olefins, halogenated hydrocarbons, oxygen-containing hydrocarbons, aromatic hydrocarbons, and other volatile substances. In addition, according to Code for indoor environmental pollution control of civil building engineer (GB50325-2001), volatile organic compounds refer to organic compounds that can participate in gas-phase photochemical reactions.

Volatile organic compounds participate in a series of complex reactions in the atmosphere to generate ozone. Specifically, after the volatile organic compounds are oxidized in the atmosphere, the reaction between $O_3$ and NO is inhibited, and free radicals are generated to accelerate conversion of NO to $NO_2$, thereby leading to rapid accumulation of $O_3$ and the deterioration of air quality. In addition, the volatile organic compounds may also be converted into secondary organic aerosols (SOAs) under certain conditions. The SOAs may also affect the atmospheric visibility and affect a regional environment through long-distance conveying. In addition, most of the volatile organic compounds are greenhouse gases, which may lead to global warming. The volatile organic compounds are also harmful to human health. When exceeding a certain concentration, the volatile organic compounds may stimulate people's eyes and respiratory tract, causing skin allergies, sore throat, and fatigue. The volatile organic compounds can very easily damage a central nervous system by means of blood-brain disorders. The volatile organic compounds harm people's liver, kidneys, brain and nervous system. The volatile organic compounds also have carcinogenicity, teratogenicity, and reproductive system toxicity.

With the implementation of China's environmental protection policy in 2018, municipalities directly under the central government, provincial capitals and cities specifically designated in the state plan among key cities successively performed automatic monitoring of volatile organic compounds. In the monitoring scheme, it is stipulated that the volatile organic compounds to be monitored manually include 117 components, and there is no mandatory requirement for the components to be monitored automatically. Currently, with the development of technology, automatic monitoring will gradually be included in the scope of supervision, which lays a solid foundation for achieving the vision of "blue sky dream". However, the volatile organic compounds themselves in the ambient atmosphere have a low concentration, a wide range, many types and rapid concentration changes, and are likely to be affected by weather and climate changes such as wind power, wind direction, rain and snow, and thus there are high requirements on analysis.

Currently, the technical principle of monitoring volatile organic compounds is gas chromatography, and a detector includes a flame ionization detector (FID), a mass spectrometry detector (MSD), etc. Since the volatile organic compounds in the ambient atmosphere have a very low concentration, it is necessary to first concentrate and enrich the volatile organic compounds into an adsorption apparatus at a low temperature by means of a thermal desorption instrument, then desorb the concentrated volatile organic compounds from the adsorption apparatus by heating, and finally introduce the volatile organic compounds into a gas chromatography-mass spectrometry (GC-MS) combined system for detection.

During the low-temperature concentration by means of the thermal desorption instrument, water vapor in a sample gas will form condensed water due to low temperature and then freeze. This will adversely cause a decrease in the adsorption efficiency of an adsorbent. In addition, some volatile organic compounds that are easily soluble in water will also be dissolved in the condensed water, resulting in a decrease in the overall concentration efficiency. More seriously, if in a place with a high humidity, ice blockage may even be caused at some parts of the thermal desorption instrument because of the too high humidity, thereby making the entire automatic monitoring system unable to operate normally. In addition, excessive water vapor may also accelerate the pollution of an ion source of a mass spectrometry detector (MSD) configured to detect volatile organic compounds.

A method of adding a gas desiccant to a gas detection path has been used in the industry for dehydration. For example, a Nafion tube (perfluorosulfonic acid resin) is used to dry a gas to be detected and filter out moisture from the sample gas. However, most desiccants have a certain degree of adsorption to some volatile organic compounds themselves, which will lead to the loss of some components from the sample, thereby leading to the distortion of a detection result.

In recent years, a dehydration scheme has also been provided, in which an independent dehydration unit is provided, and low-temperature condensation dehydration is performed by means of the dehydration unit. The sample gas having undergone dehydration is connected to a concentration unit by means of a high-temperature heat tracing pipe. An adsorption tube in the concentration unit is filled with an adsorbent, so that volatile organic compounds to be detected can be adsorbed at a low temperature, and then the volatile organic compounds in the sample are desorbed by heating to the subsequent GC-MS system for analysis.

However, there is still a need in the industry to dehydrate the sample gas containing volatile organic compounds more effectively, so as to improve the adsorption and concentration efficiency. In addition, it is also desirable to make the design of an entire gas path more compact and achieve multiple functions.

SUMMARY OF THE INVENTION

The present invention provides a gas detection device for detecting volatile organic compounds in a sample gas, the gas detection device comprising: a dehydration unit configured to dehydrate the sample gas flowing into the dehydration unit by condensation, the dehydration unit comprising a first port; a concentration unit arranged downstream of the dehydration unit in a flow direction of the sample gas and in fluid communication with the dehydration unit, the concentration unit comprising a second port; and a temperature control unit for controlling a temperature, wherein the gas detection device may have a sampling mode, in which the sample gas flows into the dehydration unit through the first port and flows out of the concentration unit through the second port, wherein the volatile organic compounds in the sample gas are concentrated in the concentration unit, and the temperature control unit may be configured such that the temperature of the sample gas after flowing out from the dehydration unit and before flowing into the concentration unit is not greater than a first preset temperature set by the temperature control unit for the concentration unit.

With the gas detection device described above, generation of condensed substances (e.g., condensed water, ice, and an ice-water mixture) in the sample gas can be effectively avoided in a simple manner after the sample gas flows into the concentration unit, thereby further preventing the resulting ice blockage. Therefore, the adsorption efficiency in the concentration unit can be improved, and thus the analysis accuracy of the volatile organic compounds can be improved.

Advantageously, the temperature control unit may comprise a cooling apparatus that can cool an entire sample gas flow path from the dehydration unit to the concentration unit. The cooling of the dehydration unit, the concentration unit and a connecting portion (if any) therebetween can be easily implemented by cooling the entire gas path, so as to generate a low temperature that facilitates dehydration from the sample gas in the sampling mode, and to prevent the water vapor in the sample gas from being condensed in the concentration unit by means of a simple structure.

Preferably, the temperature control unit may comprise a first heating apparatus for heating the dehydration unit and/or a second heating apparatus for heating the concentration unit. The arrangement of the separate heating apparatuses for the dehydration unit and the concentration unit can flexibly provide the possibility of setting the dehydration unit and the concentration unit to different temperatures.

In some embodiments, the temperature control unit may be configured to make the first preset temperature greater than a second preset temperature set for the dehydration unit by a first temperature difference, wherein the first temperature difference may be 0° C. to 10° C., and the second preset temperature may be in the range of −45° C. to −35° C.

By making the first preset temperature equal to or greater than the second preset temperature, it can be ensured that the water vapor in the sample gas that has not been condensed and dehydrated by the dehydration unit will not be condensed into water or ice in the concentration unit due to its lower internal temperature (than that of the dehydration unit), so that the impact on an adsorption effect of the concentration unit can be significantly reduced and/or the possibility of ice blockage in the concentration unit can be significantly reduced.

In addition, the gas detection device may further comprise an analysis unit for analyzing the volatile organic compounds, and may have a desorption mode, in which a carrier gas may flow into the concentration unit from the second port, such that the volatile organic compounds desorbed from the concentration unit may flow to the analysis unit with the carrier gas. By using the same port to achieve different functions in different modes (that is, the second port can be used for the outflow of the sample gas in the sampling mode, and for the inflow of the carrier gas in the desorption mode), the gas detection device with a very compact structure can be produced.

In particular, the gas detection device may comprise a capillary tube. The capillary tube may comprise a first open end and a second open end. The first open end may be in communication with the analysis unit, and the second open end may be in fluid communication with an interior of the concentration unit. In the desorption mode, the carrier gas loaded with the volatile organic compounds can flow to the analysis unit through the capillary tube.

Since the capillary tube generally has a small diameter, when the carrier gas is supplied to the analysis unit through the small-diameter capillary tube, a relatively central part (viewed from a radial cross-section) of the carrier gas containing the volatile organic compounds that flows through the concentration unit can be delivered to the capillary tube and thus to the analysis unit, so as to reduce the adverse impact of an inner wall of the concentration unit or the dehydration unit on the precision of the carrier gas containing the volatile organic compounds to be analyzed. In addition, since the capillary tube has a relatively small diameter, a flow rate or total amount of the carrier gas containing the volatile organic compounds that enters the analysis unit can be controlled.

Advantageously, the second open end may be located inside the dehydration unit, such that in the desorption mode, the carrier gas containing the volatile organic compounds can flow into the capillary tube inside the dehydration unit, wherein a part of the carrier gas can be branched off by means of the first port and/or other ports of the dehydration unit.

By branching off the carrier gas containing the volatile organic compounds, the flow rate or total amount of the carrier gas supplied to the analysis unit can be easily controlled to adapt to a processing speed of the analysis unit, thus improving the analysis precision. It can be understood that a part of the carrier gas can be branched off by means of the first port, while the other part is branch offed by means of all the ports of the dehydration unit except the first port, but it is also possible to branch off the carrier gas only by means of the first port or only by means of all the ports of the dehydration unit except the first port. The present invention provides a plurality of flexible structures for branch-off.

In addition, the gas detection device may further include a purge mode, in which the temperature control unit can heat the dehydration unit to convert the condensed substances therein into water vapor, such that the water vapor can be blown out from the dehydration unit. By using the purge mode to achieve the function of regular dehydration, the impact of water vapor on current and/or next sampling analysis can be avoided, thus improving the analysis accuracy of the volatile organic compounds.

Particularly advantageously, the gas detection device may comprise one tube, which may comprise a first tube portion constituting the dehydration unit and a second tube portion constituting the concentration unit. By integrating the two independent functions of dehydration and concentration using one simple tube, a compact structure can be achieved (e.g., a distance between the dehydration unit and the concentration unit is shortened) and the temperatures of the two units can be easily controlled (e.g., the possibility of uneven temperature control is reduced).

In particular, the one tube may be a straight tube. When this tube is constructed as a straight tube, the connecting portion (if any) between the dehydration unit and the concentration unit is also a part of the straight tube, so that the temperature control of the connecting portion can be ensured more easily, the possibility of temperature re-rising before the concentration unit can be reduced in the sampling mode, and the carrier gas containing the volatile organic compounds can be more easily controlled to flow from the concentration unit to the analysis unit in the desorption mode.

In some other embodiments, the gas detection device may comprise a first tube constituting the dehydration unit and a second tube constituting the concentration unit, the first tube may have a diameter greater than that of the second tube, the second tube may be arranged in the first tube, and a communication portion may be formed on the second tube, such that the sample gas flowing into the first tube can flow into the second tube through the communication portion.

A very compact design can be obtained by achieving the functions of dehydration and concentration by using a tube-in-tube structure. More importantly, since the second tube as the concentration unit is located in the first tube as the dehydration unit, the temperature of the concentration unit can be slightly greater than that of the dehydration unit in the sampling mode without the need for an additional separate heating apparatus by means of a gap space between the first tube and the second tube. The arrangement of the communication portion can also make the connecting portion between the two units very compact, so as to avoid the generation of condensed substances (such as condensed water, ice, and an ice-water mixture) inside the concentration unit due to a temperature re-rising point on the connecting portion between the two units.

Preferably, the second heating apparatus may comprise a heat generating mechanism (e.g., an electric heating wire) arranged around the concentration unit and a fixing mechanism (e.g., an insulating sleeve such as a ceramic sleeve and a glass tube sleeve) arranged outside the heat generating mechanism and configured to fix the heat generating mechanism. The second heating apparatus can be easily implemented by means of the heat generating mechanism arranged around the concentration unit. In addition to providing an insulation function, the insulating sleeve can further help to improve the movement flexibility of the heat generating mechanism relative to the concentration unit (e.g., the adsorption tube).

Further advantageously, the dehydration unit may comprise a reduced-diameter portion that has a reduced diameter in the flow direction of the sample gas. In the sampling mode, the sample gas may flow out of the dehydration unit through the reduced-diameter portion, while in the desorption mode, a part of the carrier gas can flow into the dehydration unit through the reduced-diameter portion for branch-off Since the reduced-diameter portion of the dehydration unit is located near a branch-off point, the reduced-diameter portion can effectively prevent the carrier gas containing the volatile organic compounds from diffusing (radially) when flowing through the dehydration unit for branch-off. In addition, the possibility of bringing the condensed substances (such as condensed water, ice, and an ice-water mixture) into the concentration unit or the connecting portion between the concentration unit and the dehydration unit can also be reduced by means of such a reduced-diameter portion in the sampling mode.

The present invention further provides a method for detecting volatile organic compounds in a sample gas by using a gas detection device. The gas detection device may comprise a dehydration unit with a first port and a concentration unit with a second port. The method may comprise a sampling step, in which the sample gas flows into the dehydration unit through the first port and flows out of the concentration unit through the second port. The sampling step may comprise: dehydrating the sample gas by condensation in the dehydration unit; concentrating the volatile organic compounds in the sample gas in the concentration unit; and controlling a temperature of the sample gas, such that the temperature of the sample gas after flowing out from the dehydration unit and before flowing into the concentration unit is not greater than a first preset temperature set for the concentration unit.

With the gas detection method described above, generation of condensed substances (e.g., condensed water, ice, ice crystals, and an ice-water mixture) in the sample gas can be effectively avoided after the sample gas flows into the concentration unit, thereby further preventing the resulting ice blockage. Therefore, the adsorption efficiency in the concentration unit can be improved, and thus the analysis accuracy of the volatile organic compounds can be improved.

Preferably, the sampling step may further comprise: controlling the temperature of the sample gas to make the first preset temperature greater than a second preset temperature set for the dehydration unit by a first temperature difference, wherein the first temperature difference may be 0° C. to 10° C., and the second preset temperature may be in a range of −45° C. to −35° C.

Advantageously, the method may comprise a purge step performed after the sampling step. The purge step may comprise: heating the dehydration unit to convert the condensed substances therein into water vapor, and blowing the water vapor out from the dehydration unit.

In addition, the gas detection device may further comprise an analysis unit for analyzing the volatile organic compounds. The method may comprise a desorption step performed after the sampling step. The desorption step comprises: heating the concentration unit to desorb the volatile organic compounds, and causing a carrier gas to flow through the concentration unit to carry the desorbed volatile organic compounds away from the concentration unit and deliver the desorbed volatile organic compounds into the analysis unit.

BRIEF DESCRIPTION OF THE DRAWINGS

Other features and advantages of the present invention will become apparent from the detailed description with reference to the accompany drawings, in which.

LIST OF REFERENCE NUMERALS

Figure 1:
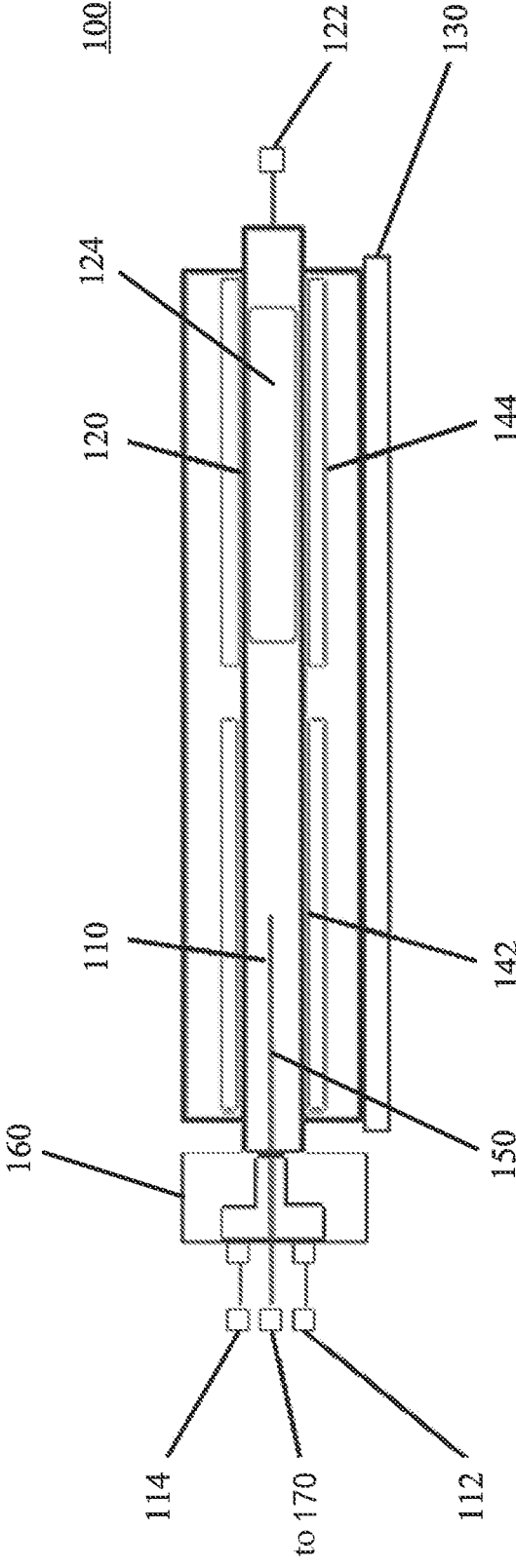
FIG. 1 shows a schematic diagram of a principle of a gas detection device according to a first embodiment of the present invention.

100 Gas detection device;
110 Dehydration unit;
112 First port;
113 Third port;
114 Branch-off port;
116 Reduced-diameter portion;
118 Extension tube;
120 Concentration unit;
122 Second port;
124 Adsorbent;
126 Communication hole;
130 Cooling apparatus;
142 First heating apparatus;
144 Second heating apparatus;
150 Capillary tube;
160 Fluid joint;
170 Analysis unit;
180 Block;
184 Second channel.

DETAILED DESCRIPTION OF EMBODIMENTS

First, the present invention relates to a gas detection device for detecting volatile organic compounds in a sample gas. Herein, the term "sample gas" refers to a gas as a sample, which contains volatile organic compounds as substances to be detected and analyzed. The sample gas may be, for example, ambient atmosphere or a gas in a closed space (e.g., a factory). Generally, at room temperature, the sample gas contains gaseous water vapor (steam). Herein, volatile organic compounds refer to compounds specified in China's national monitoring standards. In the present invention, the gas detection device can detect one or more volatile organic compounds (e.g., alkanes, olefins, halogenated hydrocarbons, oxygen-containing hydrocarbons, and aromatic hydrocarbons) according to actual requirements.

To remove (at least a part of) water vapor contained in the sample gas, the gas detection device 100 of the present invention comprises a dehydration unit 110. It can be understood that the working principle of the dehydration unit 110 of the present invention is to dehydrate the sample gas flowing into the dehydration unit by condensation. In the present invention, the term "condensation" refers to setting a low temperature (condensation temperature) for the dehydration unit 110, such that the sample gas flowing through the dehydration unit 110 can reach a temperature at which the water vapor in the sample gas can be condensed into substances (e.g., condensed water, ice, and an ice-water mixture).

It should be noted that the dehydration unit 110 of the present invention does not have to remove all the water vapor from the sample gas that flows through the dehydration unit 110, that is, the dehydration unit 110 may remove (dehydrate) only part of the water vapor from the sample gas. Advantageously, the dehydration unit 110 of the present invention can achieve the following degree of dehydration: water vapor that would significantly affect subsequent adsorption, concentration, analysis, etc. performed by the concentration unit on the volatile organic compounds in the sample gas is removed from the sample gas.

To concentrate objects to be detected in the sample gas, i.e., the volatile organic compounds, the gas detection device 100 of the present invention further comprises a concentration unit 120. As mentioned above, the concentration unit 120, e.g., an adsorption tube inside the concentration unit, may be filled with an adsorbent 124, so that the volatile organic compounds to be detected in the sample gas can be adsorbed at a low temperature. The specific arrangement of the adsorbent 124 in the concentration unit 120 and other components in the concentration unit 120 that are configured to achieve the concentration function are not limited in the present invention.

It can be understood that to remove/dehydrate the water vapor from the sample gas so as to improve concentration efficiency, the dehydration unit 110 is arranged upstream of the concentration unit 120 as viewed in a flow direction of the sample gas, that is, the dehydration unit 110 is located in front of the concentration unit 120, such that the sample gas undergoes dehydration before entering the concentration unit 120. That is to say, the sample gas flows in from the dehydration unit 110, then flows to the concentration unit 120, and flows out from the concentration unit 120. In the present invention, the process of causing the sample gas to pass through the dehydration unit 110 and the concentration unit 120 to concentrate the volatile organic compounds in the sample gas in the concentration unit 120 is referred to as a sampling step of the gas detection method or a sampling mode of the gas detection device. In the present invention, the "sampling step" or "sampling mode" also includes the dehydration for the sample gas (by the dehydration unit 110) and the concentration of the volatile organic compounds in the sample gas (by the concentration unit 120).

In the present invention, an inlet of the dehydration unit 110 for the gas to flow in may be referred to as a first port 112, and an outlet of the concentration unit 120 for the sample gas to flow out may be referred to as a second port 122. In the sampling mode, the sample gas flows into the dehydration unit 110 through the first port 112 and flows out of the concentration unit 120 through the second port 122. The volatile organic compounds in the sample gas are concentrated in the concentration unit 120. It can be understood that the term "port" does not impose any structural restrictions on the inlet of the dehydration unit 110 for the sample gas to flow in and the outlet of the concentration unit 120 for the sample gas to flow out. It can be understood that in addition to these, the dehydration unit 110 and the concentration unit 120 may further comprise other ports (which will be described in further detail below). In the present invention, the port may be closed as required (for example, based on different modes or in different steps).

In the sampling mode, after flowing out from the concentration unit 120, the sample gas may flow to a subsequent apparatus such as the sampling unit for collection, analysis or reuse of the sample gas.

The inventors of the present invention have creatively found that in a current dehydration scheme, even after the sample gas undergoes dehydration by the dehydration unit 110 at the front end, condensed substances (such as condensed water, ice, and an ice-water mixture) will still be generated in the adsorption tube of the concentration unit 120 at the rear end. In this regard, the inventors have found through research that the reasons why condensed substances still exist in the concentration unit 120 include at least the following: the water vapor in the sample gas is not completely removed in the dehydration unit 110, instead, supersaturated water vapor is generated. When the sample gas containing supersaturated water vapor is heated again after flowing out from the dehydration unit 110, an equilibrium state of saturated water vapor will be broken, so that condensation occurs again in a subsequent low-temperature concentration area.

The present invention solves the above technical problems by temperature control. Specifically, according to the present invention, any possible temperature re-rising (returning) point between the concentration unit 120 and the dehydration unit 110 is prevented by controlling the temperature of the sample gas, thereby effectively preventing the water vapor from condensing into water, ice or an ice-water mixture in the concentration unit 120 (e.g., in its adsorption tube) due to temperature reduction again after heating or temperature re-rising in the concentration unit 120, which results in that the adsorption efficiency is decreased, the concentration unit 120 is blocked by ice, and a large amount of water vapor enters the analysis unit 170 (for example, enters a gas chromatography-mass spectrometry system to damage a chromatographic column and cause accelerated pollution to a mass spectrometry ion source). More specifically, according to the present invention, the temperature of the sample gas can be controlled in the sampling mode, such that the temperature of the sample gas after flowing out from the dehydration unit 110 and before flowing into the concentration unit 120 is not greater than a first preset temperature set for the concentration unit 120. In the present invention, the term "temperature control" refers to controlling the temperature of an object to be controlled at a target temperature or within a predetermined range of the target temperature.

Advantageously, the gas detection device 100 of the present invention may comprise a temperature control unit for controlling the temperature. The temperature control unit may control the temperature of the dehydration unit 110, the concentration unit 120 or other units or components. The temperature control unit can perform very flexible temperature control. For example, the temperature control unit can provide different temperature control for a plurality of different modes of the gas detection device 100 or for various units or components in the gas detection device 100. For example, in the sampling mode of the gas detection device 100, the temperature control unit may be configured to set a first preset temperature for the concentration unit 120. In addition, the temperature control unit may be further configured to set a second preset temperature for the dehydration unit 110. However, it should be understood that the temperature control implemented by the present invention is not necessarily implemented by the temperature control unit, for example, the temperature control may be implemented or completed in an assisted manner by other structures or apparatuses than the gas detection device 100.

The temperature control unit of the present invention may be configured such that the temperature of the sample gas after flowing out from the dehydration unit 110 and before flowing into the concentration unit 120 is not greater than the first preset temperature set by the temperature control unit for the concentration unit 120. Since the dehydration unit 110 is generally at a relatively low temperature for condensation and dehydration in the sampling mode, if it can be ensured that the sample gas in the gas path between the dehydration unit 110 and the concentration unit 120 is also kept at a low temperature, the process of re-heating the sample gas before the sample gas enters the concentration unit 120 can be avoided, such that the equilibrium state of saturated water vapor cannot be broken even if the water vapor in the sample gas is not completely removed by the dehydration unit 110. In this way, the water vapor in the sample gas will not be condensed again when flowing through the concentration unit 120 that is also at a low temperature, thus improving the adsorption efficiency of the volatile organic compounds in the concentration unit 120 and the overall gas detection precision. In addition, ice blockage caused by the condensed substances (e.g., condensed water, ice, ice crystals, and an ice-water mixture) in the concentration unit 120 can also be avoided, and the service life of the concentration unit 120 can thus be prolonged.

More specifically, since the dehydration unit 110 is generally at a relatively low set temperature, it can be ensured that the sample gas about to enter the concentration unit 120 will not undergo the process of heating (temperature re-rising) provided that the sample gas in the gas path between the dehydration unit 110 and the concentration unit 120 is at a relatively low temperature. Here, the so-called "heating" does not include some temperature fluctuations caused by the precision of temperature control and other reasons. That is to say, in the present invention, even if the sample gas in the gas path between the dehydration unit 110 and the concentration unit 120 is at a temperature slightly greater than the first preset temperature of the concentration unit 120 due to various reasons, it is only temporary, and the sample gas after flowing out from the dehydration unit 110 and before flowing into the concentration unit 120 is still at a temperature not greater than the first preset temperature set by the temperature control unit for the concentration unit 120 during a main time period of the sampling mode.

In the sampling mode or other modes to be explained below, in the present invention (for example, by means of the temperature control unit), the temperature of the gas path between the dehydration unit 110 and the concentration unit 120 can also be controlled, but this does not mean that the temperature control unit needs to (specially) cool this gas path. For example, where there is a relatively small distance between the dehydration unit 110 and the concentration unit 120 or where the second preset temperature of the dehydration unit 110 is less than the first preset temperature of the concentration unit 120 (the present invention is not limited to these two cases), there is no need to (specially) cool this gas path, and the temperature of the sample gas flowing through the gas path between the dehydration unit 110 and the concentration unit 120 can meet the aforementioned configuration of the present invention provided that it is ensured that there is no significant heating.

In addition, it can be understood that when the gas detection device 100 is designed to be very compact, there may be no significant distance between the dehydration unit 110 and the concentration unit 120, that is, there is a very small gas path (or a connecting portion) or even no gas path (for example, the two units are directly adjacent to each other, one behind the other, or one above the other) between the dehydration unit 110 and the concentration unit 120. Herein, the so-called "temperature of the sample gas after flowing out from the dehydration unit 110 and before flowing into the concentration unit 120" is basically equivalent to the temperature of the sample gas flowing out from the dehydration unit 110. Since the second preset temperature of the dehydration unit 110 is generally less than the first preset temperature of the concentration unit 120, the afore-mentioned requirements of the present invention can also be met.

In addition, it can be noted that the aforementioned temperature comparison mainly involves the comparison between the temperature of the sample gas itself after flowing out from the dehydration unit 110 and before flowing into the concentration unit 120 and the first preset temperature of the concentration unit 120, rather than the comparison between the temperature of the gas path between the dehydration unit 110 and the concentration unit 120 set by the temperature control unit and the first preset temperature. This is because the temperature control unit may not (specially) cool the gas path as mentioned above. In addition, such requirements are also based on the following considerations: Due to the structure, material or arrangement of the gas path, the temperature of the sample gas flowing through the gas path (as mentioned above, the actual distance of the gas path may be zero) may be different from the temperature set by the temperature control unit for the gas path (it should be noted that the temperature control unit may not set the temperature for the gas path). In any case, it is necessary to ensure that the actual (experienced) temperature of the sample gas after flowing out from the dehydration unit 110 and before entering the concentration unit 120 is not greater than the first preset temperature of the concentration unit 120.

Advantageously, the temperature control unit of the present invention may comprise a cooling apparatus 130. Preferably, the cooling apparatus 130 includes a cooling apparatus 130 that can cool the entire sample gas flow path from the dehydration unit 110 to the concentration unit 120 (for example, in the sampling mode), thereby improving the cooling efficiency. For example, the entire sample gas flow path from the dehydration unit 110 to the concentration unit 120 can be brought to a required relatively low temperature by means of the cooling apparatus 130. For example, it is possible to simply place the dehydration unit 110, the concentration unit 120 and a pipeline or connecting portion in any form therebetween in or on the cooling apparatus 130. However, it may also be envisaged that a cooling apparatus 130 or component individually cools one or more of the dehydration unit 110, the concentration unit 120 and the pipeline or connecting portion in any form therebetween.

Further advantageously, the temperature control unit may comprise a second heating apparatus 144 for heating the concentration unit 120. In addition, the temperature control unit may also comprise a first heating apparatus 142 for heating the dehydration unit 110. This separate arrangement of the heating apparatuses can facilitate flexible temperature adjustment of the units. Especially, when the cooling apparatus 130 included in the temperature control unit is configured to cool the entire sample gas flow path from the dehydration unit 110 to the concentration unit 120, that is, the cooling temperature provided for the entire gas path is the same or basically the same, different temperatures of the units can be very easily controlled by the separately arranged heating apparatuses. Advantageously, the heating apparatus can heat to a relatively high temperature in a short time, for example, the temperature can be increased by 300° or above in a dozen seconds.

In some embodiments, the second heating apparatus 144 may comprise a heat generating mechanism (e.g., a heating wire or a heating sheet) arranged around the concentration unit 120, especially in contact with the concentration unit (e.g., attached to the concentration unit 120), and a fixing mechanism arranged outside the heat generating mechanism to fix the heat generating mechanism. The fixing mechanism is preferably constructed as an insulating sleeve, such as a ceramic sleeve and a glass sleeve, to provide an insulating function. The insulating sleeve can further help to improve movement flexibility of the heat generating mechanism relative to the concentration unit (e.g., the adsorption tube).

In the present invention, the temperature control unit may be configured to make the first preset temperature set for the concentration unit 120 greater than the second preset temperature set for the dehydration unit 110 by a first temperature difference. The first temperature difference may be 0° C. or greater than 0° C., such as 0-10° C. In other words, the first preset temperature may be equal to or greater than the second preset temperature. When the first preset temperature is equal to or greater than the second preset temperature, it can be ensured that the water vapor in the sample gas that has not been condensed and removed/dehydrated by the dehydration unit 110 will not be condensed into water, ice or an ice-water mixture in the concentration unit 120 due to its lower internal temperature (than that of the dehydration unit 110), so that the adverse impact on an adsorption effect of the concentration unit 120 can be significantly reduced and/or the possibility of ice blockage in the concentration unit 120 can be significantly reduced. Even if one cooling apparatus 130 is used to cool both the dehydration unit 110 and the concentration unit 120 in the sampling mode, the actual temperature of the dehydration unit 110 may be greater than that of the concentration unit 120 due to uneven conduction of the cooling apparatus 130. In some embodiments, the second preset temperature may be between −45° C. and −35° C., such as −40° C. The first preset temperature may be between −40° C. and −30° C. or between −35° C. and −30° C. It can be understood that in the sampling step of the gas detection method of the present invention, the temperature of the sample gas can be controlled, such that the first preset temperature is greater than the second preset temperature by the aforementioned first temperature difference, but the temperature control is not implemented by the temperature control unit. It should be understood that the first preset temperature of the present invention may be other temperatures suitable for concentration besides the aforementioned temperature range.

In some embodiments, in the sampling mode, the temperature control unit may cool at least the dehydration unit 110 and the concentration unit 120, such that at least the dehydration unit 110 and the concentration unit 120 (preferably the entire gas path from the dehydration unit 110 to the concentration unit 120) are kept at a low temperature. On this basis, when the temperature control unit comprises the second heating apparatus 144 for heating the concentration unit 120, the concentration unit 120 can be heated to a temperature slightly greater than that of the dehydration unit 110, for example, by 1-10° C., especially 3-7° C., such as 5° C. When the temperature control unit comprises both the second heating apparatus 144 and the first heating apparatus 142 mentioned above, the first preset temperature of the concentration unit 120 may also be (slightly) greater than the second preset temperature of the dehydration unit 110 by heating the dehydration unit 110 and the concentration unit 120 to different temperatures respectively. However, as mentioned above, making the first preset temperature equal to the second preset temperature also falls within the scope of protection of the present invention.

However, it can be understood that the temperature control unit of the present invention may not comprise the cooling apparatus 130 and the heating apparatuses that are separately arranged (that is, cooling and heating are not superimposed), but directly adjust their temperatures to their respective required temperatures. In other words, the cooling apparatus 130 and the heating apparatuses do not operate simultaneously, but, for example, directly cool the dehydration unit 110 and the concentration unit 120 to the second preset temperature and the first preset temperature respectively. For example, the temperature control unit may directly adjust the temperature of the dehydration unit 110 to between −45° C. and −35° C. in the sampling mode, and directly adjust the temperature of the concentration unit 120 to be 0-10° C. greater than the aforementioned temperature of the dehydration unit 110.

The gas detection device 100 of the present invention further comprises an analysis unit 170 for analyzing the volatile organic compounds, such as a gas chromatography-mass spectrometry (GC-MS) system. Before the volatile organic compounds are delivered to the analysis unit 170 for analysis, it is necessary to first desorb the volatile organic compounds concentrated in the concentration unit 120. To this end, the gas detection device 100 may include a desorption mode or the gas detection method may include a desorption step. In this desorption mode or in the desorption step, a carrier gas may be delivered into the concentration unit 120 (for example, through the second port 122 of the concentration unit 120). As the carrier gas flows through the concentration unit 120, the volatile organic compounds desorbed from the concentration unit 120 can flow to the analysis unit 170 together with the carrier gas. Advantageously, the sample gas flows out through the second port 122 of the concentration unit 120 in the sampling mode, and the carrier gas flows into the concentration unit 120 through the second port 122 in the desorption mode. However, it is also conceivable that the port for the sample gas to flow out from the concentration unit 120 and the port for the carrier gas to flow into the concentration unit 120 are not the same port of the concentration unit 120. In the desorption mode, the second port 122 of the concentration unit 120 may be in communication with an injection unit to deliver the carrier gas into the concentration unit 120.

In the present invention, the carrier gas is generally a gas that does not chemically react with the volatile organic compounds. The carrier gas should not be a gas that affects qualitative or quantitative analysis performed by the analysis unit 170 on the volatile organic compounds. For example, the carrier gas itself does not contain volatile organic compounds. Therefore, the carrier gas is preferably an inert gas, such as helium or nitrogen.

In the desorption mode, the temperature of the concentration unit 120 is generally raised from a low temperature to a relatively high temperature, such as 250-300° C., at which the volatile organic compounds adsorbed in the concentration unit (in the sampling mode) can be desorbed. For example, the temperature control unit (e.g., the second heating apparatus 144) may heat the concentration unit 120 to desorb the volatile organic compounds.

In addition, in the desorption mode, the carrier gas containing the volatile organic compounds may not entirely flow into the analysis unit 170, but only part of the carrier gas flows into the analysis unit 170, so that the carrier gas can enter the analysis unit 170 at a desired flow rate. To this end, the gas detection device 100 of the present invention may further include a design for branching off the carrier gas to control the flow rate of the carrier gas supplied to the analysis unit 170 (which will be further described below).

Before the gas detection device 100 enters the desorption mode (from the sampling mode), optionally, the gas detection device 100 includes a purge mode or the gas detection method includes a purge step. In the purge mode or in the purge step, the dehydration unit 110 is heated to such an extent that condensed substances (e.g., condensed water, ice, ice crystals, and an ice-water mixture) in the dehydration unit can be converted into water vapor, and the water vapor is blown out of the dehydration unit 110, thereby dehydrating the condensed substances accumulated in the dehydration unit 110. Preferably, the dehydration unit 110 undergoes the heating by means of the temperature control unit. For example, in the purge mode, the dehydration unit 110 may be heated to 100-200° C., but a different temperature may also be envisaged. Herein, a purge gas may be any suitable type of gas, but at least should not be a gas that affects qualitative or quantitative analysis performed by the analysis unit 170 on the volatile organic compounds. For example, the purge gas itself does not contain volatile organic compounds. For example, the flow rate of the purge gas may be 100-150 ml/min.

The purge mode or step is advantageous, because the purge mode or step can ensure that there are very few condensed substances (for example, condensed water, ice, and ice crystals) accumulated in the dehydration unit 110 before the sampling mode is entered next time, so as to prevent excessive condensed substances from accumulating in the dehydration unit to cause possible ice blockage or affect the performance of the dehydration unit 110. In addition, in some embodiments, in the desorption mode, the carrier gas flowing through the concentration unit 120 to carry the volatile organic compounds may also flow through the dehydration unit 110 after leaving the concentration unit 120 and before flowing into the analysis unit 170. In this case, if purging is performed before the desorption mode, it can also be ensured that in the desorption mode, the carrier gas will not adversely carry condensed substances or water vapor into the analysis unit 170 again when passing through the dehydration unit 110, otherwise the accuracy of an analysis result will be seriously affected. That is to say, by using the purge step or the purge mode to achieve the function of regular dehydration, the impact of water vapor on current and/or next sampling analysis can be avoided.

More preferably, in the purge mode, in addition to heating the dehydration unit 110, it is also possible to heat the concentration unit 120 (for example, by means of the second heating apparatus 144), such that very little water vapor that may exist in the concentration unit 120 is also blown out from the port of the dehydration unit 110 or other ports of the gas detection device 100 with the purge gas.

Figure 2:
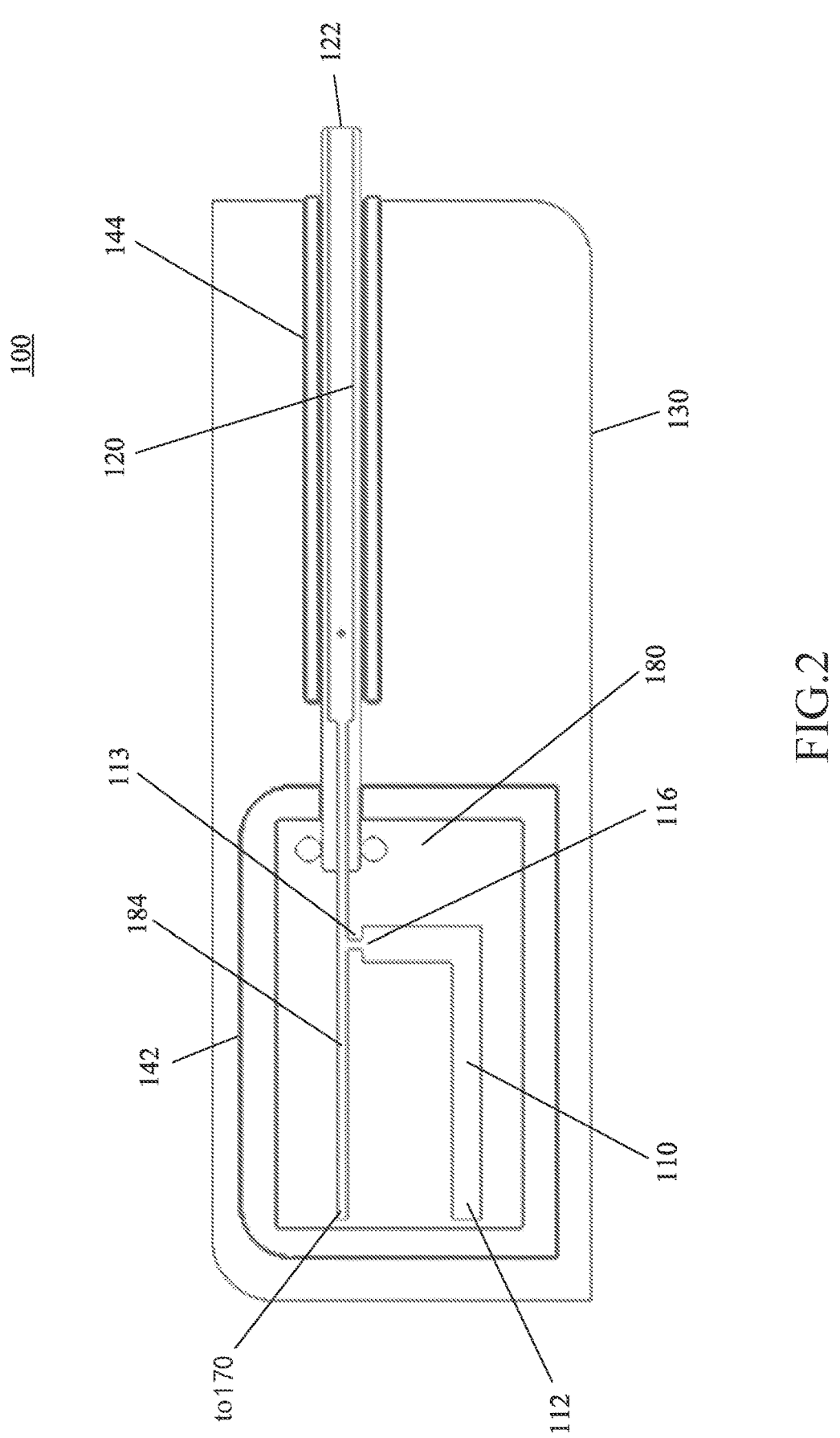
FIG. 2 shows a schematic diagram of a principle of a gas detection device according to a second embodiment of the present invention.
Figure 3:
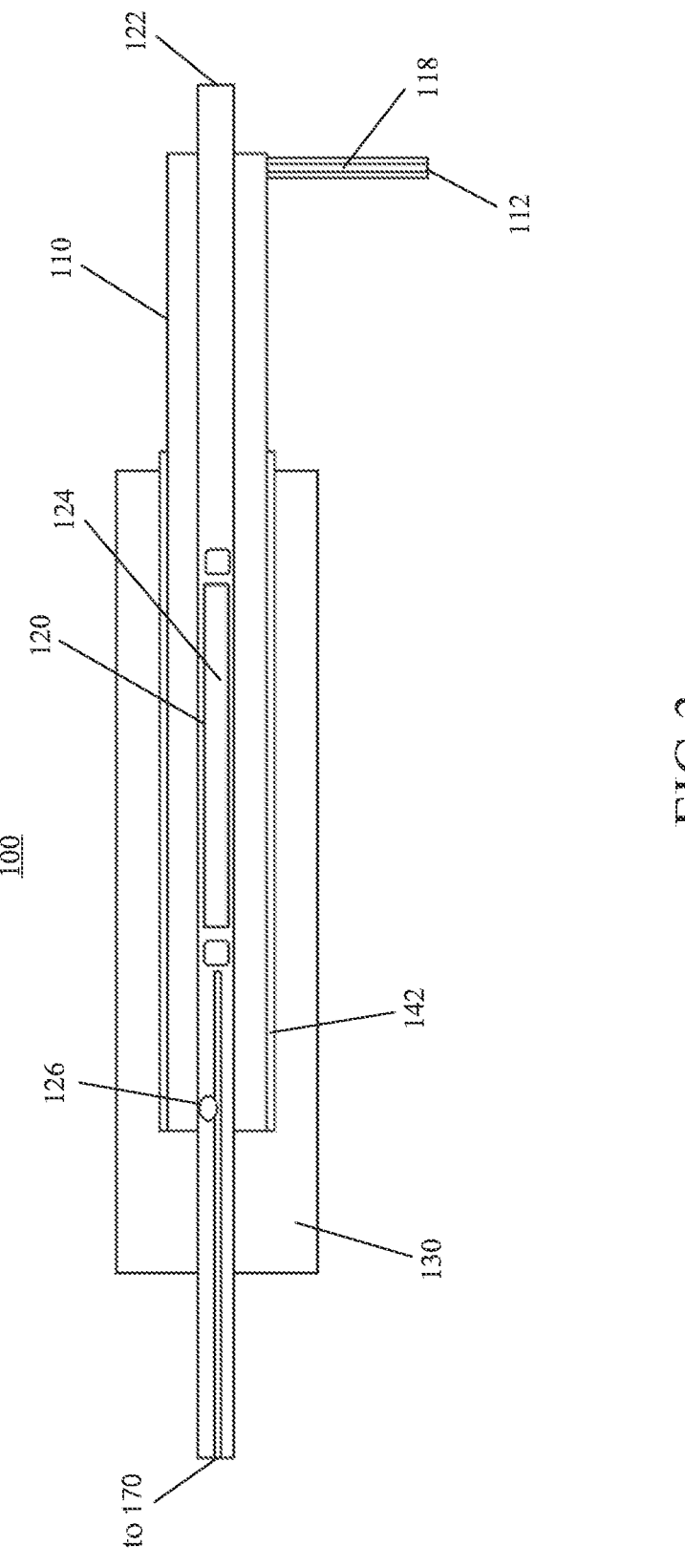
FIG. 3 shows a schematic diagram of a principle of a gas detection device according to a third embodiment of the present invention.

The gas detection device 100 and the gas detection method according to various embodiments of the present invention will be further explained with reference to FIGS. 1-3 below. However, it should be understood that the description with reference to FIGS. 1-3 does not mean that the present invention is limited to the specific structures shown in the drawings, unless the embodiments shown in FIGS. 1-3 are explicitly indicated herein. In addition, the features of various embodiments of the present invention can be interchanged, unless it is explicitly indicated herein that the features are only special features of one embodiment.

In a first embodiment shown in FIG. 1, the gas detection device 100 comprises a dehydration unit 110 and concentration unit 120. As viewed in the flow direction of the sample gas in the sampling mode, the dehydration unit 110 is located upstream of the concentration unit 120, that is, the sample gas flows from the dehydration unit 110 to the concentration unit 120. In the first embodiment, the dehydration unit 110 and the concentration unit 120 are formed from one tube. Herein, the tube comprises a first tube portion for constituting the dehydration unit 110 and a second tube portion for constituting the concentration unit 120. Preferably, the tube is a straight tube. However, it can be understood that the embodiment of one tube also covers the case where different portions of the tube have different diameters. That is, the present invention is not limited to the case where one tube has a constant diameter shown in FIG. 1.

Particularly preferably, the tube is a quartz glass tube. When the dehydration unit 110 and/or the concentration unit 120 are formed from the quartz glass tube or another type of glass tube (e.g., an organic glass tube), the risk of adsorbing the sample gas to a tube wall can be avoided as much as possible, thereby improving the analysis precision of the volatile organic compounds in the sample gas.

Since the dehydration unit 110 and the concentration unit 120 may be formed from one tube, especially one straight tube, a gas path between the dehydration unit 110 and the concentration unit 120 is also a part of the same tube. However, it can be understood that the tube may comprise only the first tube portion for constituting the dehydration unit 110 and the second tube portion for constituting the concentration unit 120. This means that the distance between the dehydration unit 110 and the concentration unit 120 is zero. However, it can also be understood that the tube may also comprise other portions in addition to the first portion and the second portion, especially a connecting portion between the two portions. However, it can be understood that the dehydration unit 110 and the concentration unit 120 of the present invention may, of course, also be apparatuses or structures independent of each other. In this case, the dehydration unit and the concentration unit may be in fluid communication with each other by means of an intermediate connecting portion.

In the first embodiment, the first port 112 is one of a plurality of ports (three are shown in FIG. 1, but the number of ports is not limited thereto) of the dehydration unit 110 on a left side (i.e., a sample gas inflow side in the sampling mode), and the second port 122 is a port of the concentration unit 120 on a right side (i.e., a sample gas outflow side in the sampling mode). In addition, when the dehydration unit 110 and the concentration unit 120 are of structures independent of each other, the dehydration unit 110 may comprise another port leading to the concentration unit 120, and the concentration unit 120 may also comprise another port leading to the dehydration unit 110.

Advantageously, the dehydration unit 110 further comprises other ports in addition to the first port 112 for the inflow of the sample gas. For example, the dehydration unit 110 may comprise a port for communication with the analysis unit 170, such that the carrier gas containing the volatile organic compounds is delivered to the analysis unit 170 by means of the port in the desorption mode. For another example, the dehydration unit 110 may comprise a port for the inflow of a purge gas. For still another example, the dehydration unit 110 may comprise a port (i.e., a branch-off port 114) for branching off the carrier gas containing the volatile organic compounds. It can be understood that various functions of the dehydration unit 110 can be achieved by the same port. For example, the port in communication with the analysis unit 170 and the port for the inflow of the purge gas may be the same port. For another example, the port for branching off the carrier gas and the port for the outflow of the purge gas from the dehydration unit 110 in the purge mode may be the same port. However, it should be understood that in one mode, one port can generally only be used to achieve one function.

Preferably, when the dehydration unit 110 comprises a plurality of ports, the plurality of ports may be integrated into a fluid joint 160, but this is not necessary. As shown in FIG. 1, three ports are integrated into a T-joint (e.g., a tee structure), and the T-joint is in fluid communication with a body of the dehydration unit 110, but this is only illustrative. More preferably, the fluid joint 160 is arranged in a constant temperature area without being cooled in the sampling mode or being heated in the purge or desorption mode. For example, the fluid joint 160 may be arranged in a constant temperature area at 120° C. to avoid condensation of the sample gas before the sample gas enters the dehydration unit 110, and to avoid relatively large temperature fluctuations (large temperature fluctuations will lead to unnecessary air tightness failure). In the present invention, the temperature of the constant temperature area is not limited to the temperature listed herein.

In addition, although the concentration unit 120 shown in FIG. 1 only comprises the second port 122 on the right side for the inflow of the carrier gas, the concentration unit 120 may also comprise other ports (not shown) in addition to the second port to achieve more functions.

It can be understood that when the gas detection device 100 is in the sampling mode, the ports of the dehydration unit 110 for achieving other functions except the first port 112 (if any, and the port leading to the concentration unit 120) are closed. When the gas detection device 100 is in the purge mode, all the ports of the dehydration unit 110 except the port for the inflow of the purge gas and the port for the outflow of the purge gas are closed. In this case, if the dehydration unit 110 is still in fluid communication with the concentration unit 120, the second port 122 of the concentration unit 120 (if any, and other ports of the concentration unit 120) is also closed to prevent the purge gas from flowing out from the concentration unit 120. When the gas detection device 100 is in the desorption mode, the port of the dehydration unit 110 in communication with the analysis unit 170 is open, or the dehydration unit and the analysis unit are kept in fluid communication with each other. In this case, if it is necessary to branch off the carrier gas containing the volatile organic compounds, the port of the dehydration unit 110 for branching off the carrier gas is also open, while the other ports of the dehydration unit 110, such as the first port 112 for the inflow of the sample gas, are closed.

In a preferred embodiment, the gas detection device 100 may further comprise a capillary tube 150 or another form of pipeline having a diameter less than that of the dehydration unit 110. When the gas detection device 100 comprises a capillary tube 150, the capillary tube 150 comprises a first open end and a second open end. The first open end is in communication with the analysis unit 170, and the second open end is in fluid communication with an interior of the concentration unit 120. In the desorption mode, the carrier gas carrying the volatile organic compounds may flow to the analysis unit 170 through the capillary tube 150. In the purge mode, the first open end may also be used as a port for introducing the purge gas.

In the first embodiment, the second open end of the capillary tube 150 extends into the dehydration unit 110. For example, the second open end of the capillary tube 150 may be located near the concentration unit 120, at a middle position in the dehydration unit 110 in an axial direction or at other positions inside the dehydration unit 110. When the second open end is located inside the dehydration unit 110, in the desorption mode, the carrier gas containing the volatile organic compounds flows into the capillary tube 150 inside the dehydration unit 110 and, in turn, to the analysis unit 170. Alternatively, however, the second open end of the capillary tube 150 may not be located inside the dehydration unit 110, but inside the concentration unit 120, for example, at or near the end of the concentration unit 120 facing the dehydration unit 110. In this case, the carrier gas containing the volatile organic compounds has flowed into the capillary tube 150 inside the concentration unit 120.

When the carrier gas is supplied to the analysis unit 170 through the capillary tube 150 with a small diameter, transverse diffusion of the carrier gas containing the volatile organic compounds can be reduced compared with when no capillary tube 150 is provided, thereby reducing the impact on precision. Since the second open end of the capillary tube 150 (i.e., the end that allows the carrier gas to flow into the capillary tube 150) is generally located inside the concentration unit 120 or the dehydration unit 110, especially at a relatively central position in a radial direction, a relatively central part (viewed from the radial section) of the carrier gas containing the volatile organic compounds that flows through the concentration unit 120 can be delivered to the capillary tube 150 and thus to the analysis unit 170, so as to reduce the impact of an inner wall (e.g., a tube wall) of the concentration unit 120 or the dehydration unit 110 on the precision of the carrier gas containing the volatile organic compounds to be analyzed. In addition, since the capillary tube 150 has a relatively small diameter, a flow rate or total amount of the carrier gas containing the volatile organic compounds that enters the analysis unit 170 can be controlled. For example, the carrier gas can be kept at a relatively low flow rate or at a flow rate adapted to a processing speed of the analysis unit 170.

To better control the flow rate or total amount of the carrier gas containing the volatile organic compounds that enters the analysis unit 170, as mentioned above, in the desorption mode, a part of the carrier gas can be branched off (for example, by means of the port for branch-off) so as not to flow into the analysis unit 170. In some embodiments, a branch-off rate may be set to 1:5, that is, when the flow rate of the carrier gas entering the analysis unit 170 is 1.2 ml/min, the flow rate at the port for branch-off is 6 ml/min, but the present invention is not limited thereto. In the first embodiment, the port for branch-off is the uppermost port on the left side shown in FIG. 1, rather than the first port 112 for the inflow of the sample gas in the sampling mode.

As shown in FIG. 1, a relatively radial central part of the carrier gas containing the volatile organic compounds that flows through the concentration unit 120 flows into the capillary tube 150, while the other relatively peripheral part flows out through another port of the dehydration unit 110. However, it can be understood that in the present invention, it is not necessary to choose to deliver the central part of the carrier gas to the analysis unit 170, but this is only a preferred solution, and it is also not necessary to ensure that only a relatively (radial) central part of the carrier gas can be delivered to the capillary tube 150 when the capillary tube 150 is employed.

In the first embodiment, in the purge mode, the purge gas flows into the dehydration unit 110 from the middle port located on the left in FIG. 1 and flows out from the first port 112 of the dehydration unit 110, so as to blow away water or water vapor from the dehydration unit 110 by means of the purge gas. It can be understood that in the first embodiment, the port for the inflow of the purge gas is just the port in communication with the analysis unit 170 and the capillary tube 150 in the desorption mode, but the present invention is not limited thereto. For example, the ports may be separate ports. In addition, as mentioned above, in the purge mode, the second port 122 on the right side of the concentration unit 120 shown in FIG. 1 is closed.

FIG. 1 further shows a temperature control unit of the gas detection device 100. The temperature control unit comprises a cooling apparatus 130. The cooling apparatus 130 cools the entire gas path from the dehydration unit 110 to the concentration unit 120. It can also be seen that the temperature control unit comprises a first heating apparatus 142 for heating the dehydration unit 110 and a second heating apparatus 144 for heating the concentration unit 120. The first heating apparatus 142 and the second heating apparatus 144 are respectively arranged around the dehydration unit 110 and the concentration unit 120, while the cooling apparatus 130 is arranged below the entire gas path from the dehydration unit 110 to the concentration unit 120. In this embodiment, in the sampling mode, the same low temperature, e.g., $-45°$ C. to $-35°$ C., can be set for the entire gas path from the dehydration unit 110 to the concentration unit 120. By operating the second heating apparatus 144, the temperature of the concentration unit 120 can be raised to be $0$-$10°$ C. greater than that of the concentration unit 120.

In the purge mode, the first heating apparatus 142 may be used to heat the dehydration unit 110 to convert (e.g., vaporize) condensed substances (e.g., condensed water, ice, ice crystals, and an ice-water mixture) located in the dehydration unit into water vapor, for example, to heat the dehydration unit 110 to $100$-$200°$ C. In the desorption mode or desorption step, the concentration unit 120 may be heated (for example, by using the second heating apparatus 144) to desorb the volatile organic compounds concentrated in the concentration unit into the carrier gas. For example, the concentration unit 120 may be heated to $250$-$350°$ C. It should be understood that the temperature ranges listed here are merely illustrative. Usually, in the purge mode and the desorption mode, the cooling apparatus 130 of the temperature control unit does not operate.

In the second embodiment shown in FIG. 2, the dehydration unit 110 is also located upstream of the concentration unit 120 as viewed in the flow direction of the sample gas. Specifically, the dehydration unit 110 is configured in the form of a first channel, such as a first channel formed from a block 180. The concentration unit 120 is constructed in the form of a separate pipeline. The dehydration unit 110 comprises a first port 112 located at a lower portion on the left side in FIG. 2 for the inflow of the sample gas, while the concentration unit 120 comprises a second port 122 located on the right side in FIG. 2. It can be seen that in the second embodiment, the dehydration unit 110 and the concentration unit 120 are spaced apart from each other, and a connecting portion is included between the dehydration unit and the concentration unit, such that the dehydration unit and the concentration unit are in fluid communication with each other. Advantageously, the connecting portion may be supported in the block 180. In addition, an O-ring may be pressed by means of a threaded structure to achieve functions of fixing the connecting portion or the concentration unit 120 (for example, its adsorption tube) and maintaining air tightness.

In the second embodiment, a port of the dehydration unit 110 facing the concentration unit 120 is referred to a third port 113. The block 180 may be further provided with a second channel 184 in addition to the first channel. The second channel 184 comprises an end in fluid communication with the third port 113 and the concentration unit 120, and a further open end opposite to the end. The further open end may be used as a port for the carrier gas containing the volatile organic compounds to flow into the analysis unit 170 in the desorption mode, and may also be used as a port for the purge gas to flow into the block 180 and therefore the first channel (i.e., the dehydration unit 110) in the block 180 in the purge mode.

In the purge mode, the first port 112 of the dehydration unit 110 may also be used as a port for the outflow of the purge gas. In this case, the purge gas may, for example, flow into the second channel 184 in the block 180 from the further open end of the second channel 184, then flow into the interior of the dehydration unit 110 from the third port 113 of the dehydration unit 110 through the position where the second channel 184 intersects with or is in communication with the first channel, and finally flow out from the dehydration unit 110 through the first port 112 of the dehydration unit 110. In this case, the port of the concentration unit 120 is closed.

In the desorption mode, the carrier gas containing the volatile organic compounds that flows through the concentration unit 120 can flow from the further open end to the analysis unit 170 through the second channel 184 of the block 180. Since the first channel is also in fluid communication with the second channel 184, a part of the carrier gas that flows to the second channel 184 also flows to the first channel as a branch-off channel, thereby controlling the flow rate or total amount of the carrier gas delivered to the analysis unit 170.

It can be seen that the dehydration unit 110 only needs to be in fluid communication with the concentration unit 120 and located upstream of the concentration unit (as viewed in the flow direction of the sample gas in the sampling mode), rather than needing to be in a straight line with the concentration unit 120. In addition, the dehydration unit 110 itself may not be in the shape of a straight line, but may be, for example, in an L shape, a U shape or any other suitable shape. When a straight-line shape is not used, it is possible to save volume and minimize the risk of bringing the condensed substances into the concentration unit 120.

In a preferred embodiment, the dehydration unit 110 has a relatively large inner diameter, which, for example, may be 2 mm or above, preferably 3 mm. The large-diameter dehydration unit 110 (the first tube portion in the first embodiment, the first channel in the block 180 in the second embodiment, or another form of dehydration unit 110) can effectively prevent ice blockage when the sample gas has a too high humidity and there is relatively much water condensed in the dehydration unit 110.

In a more preferred embodiment, as shown in FIG. 2, the dehydration unit 110 may comprise a reduced-diameter portion 116 that has a reduced diameter in the flow direction of the sample gas. For example, the reduced-diameter portion 116 may be located at or near the third port 113 of the dehydration unit, such that the sample gas can flow out from the dehydration unit 110 through the reduced-diameter portion 116 in the sampling mode. In the desorption mode, a part of the carrier gas containing the volatile organic compounds can also flow into the dehydration unit 110 through the reduced-diameter portion 116 for branch-off Since the reduced-diameter portion 116 of the dehydration unit 110 is located near a branch-off point, the reduced-diameter portion 116 can effectively prevent the carrier gas containing the volatile organic compounds from diffusing (radially) when flowing through the dehydration unit 110 for branch-off. The diffusion would adversely cause a too wide peak width to be analyzed, resulting in a decrease in the overall analysis efficiency.

In the second embodiment, the entire gas path including the dehydration unit 110, the concentration unit 120 and the connecting portion therebetween is arranged inside the temperature control unit. The cooling apparatus 130 is arranged on the peripheries of the above units and the connecting portion to provide an overall cooling effect. In addition, the first heating apparatus 142 may be mounted around the block 180 to heat the entire block 180 including the first channel (as the dehydration unit 110) and the second channel 184. It can be seen that since at least a part of the connecting portion is supported in the block 180, the first heating apparatus 142 can also heat the connecting portion. The second heating apparatus 144 is mounted around the concentration unit 120 to heat the concentration unit.

It should be noted that if the cooling apparatus 130 provides overall cooling, the actual temperature inside the dehydration unit 110 may be greater than the temperature inside the concentration unit 120 because the dehydration unit 110 is located inside the block 180. To prevent the temperature in the concentration unit 120 from being less than that in the dehydration unit 110 to cause the generation of condensed substances (such as condensed water, ice, ice crystals, and an ice-water mixture) in the concentration unit 120, it is necessary to (slightly) raise the first preset temperature of the concentration unit 120 as mentioned above in the sampling mode, for example, by 3-5° C.

In the third embodiment shown in FIG. 3, the concentration unit 120 is configured to be located within the dehydration unit 110. For example, when the dehydration unit 110 is formed from a first tube, the concentration unit 120 is configured as a second tube located in the first tube. In other words, the dehydration unit 110 and the concentration unit 120 may be tubes independent of each other. The first tube has a diameter greater than that of the second tube. However, the second tube has a length that may be greater than that of the first tube. For example, the second tube may extend from two axial ends of the first tube. However, it should be understood that the concentration unit 120 and the dehydration unit 110 of the present invention may be constructed not in the shape of a straight tube shown in FIG. 3, but in other shapes and sizes.

In the third embodiment, in the sampling mode, the dehydration unit 110 is still located upstream of the concentration unit 120. To enable the sample gas to flow from the dehydration unit 110 into the concentration unit 120, one or more communication portions (one communication hole 126 is shown in FIG. 3) are provided or formed on the concentration unit 120. The communication portion may be in the form of the communication hole 126, but may also include other forms, such as a communication tube. Specifically, in the sampling mode, the sample gas flows in from the first port 112 of the dehydration unit 110, which is a port on the right side in FIG. 3. Herein, the sample gas flows from the right side to the left side of the dehydration unit 110, and then flows into the concentration unit 120 through the communication hole 126 near the left end of the dehydration unit. However, it should be noted that the communication hole 126 may be located at any suitable position on the concentration unit 120, rather than necessarily at the left end of the dehydration unit 110. However, in the latter case, the sample gas can flow through the dehydration unit 110 by a maximum distance to improve the dehydration effect.

Preferably, as shown in FIG. 3, an extension tube 118 is further connected outside the first port 112 of the dehydration unit 110 to facilitate flexible adjustment of a supply direction of the sample gas flowing into the dehydration unit 110 (for example, the sample gas may come from a direction perpendicular to the axial direction of the first tube constituting the dehydration unit 110), but this is not necessary.

In the third embodiment, in the desorption mode, the carrier gas flows into the concentration unit 120 from the second port 122 (i.e., the rightmost port in FIG. 3) of the concentration unit 120. The carrier gas containing the volatile organic compounds may flow out from a further open port (e.g., the leftmost port in FIG. 3) of the concentration unit 120 opposite to the second port 122. However, preferably, the carrier gas containing the volatile organic compounds is delivered to the analysis unit 170 by means of the capillary tube 150. More preferably, the second open end of the capillary tube 150 may extend into the concentration unit 120, especially to a position closer to the second port 122 of the concentration unit 120 than the communication portion. In this case, the communication portion may be used as a branch-off port in the desorption mode. The branch-off port is preferably located downstream of the second open end of the capillary tube 150 as viewed in the flow direction of the carrier gas. Therefore, a part, especially its (radial) central part, of the carrier gas containing the volatile organic compounds first flows into the capillary tube 150 while a part of the carrier gas close to an inner wall of the concentration unit 120 further flows over an outer side of the capillary tube 150 into the communication hole 126 (as a branch-off port), to further flow out from the dehydration unit 110 through the first port 112 or other ports of the dehydration unit 110. In this mode, since a positive pressure of the carrier gas is provided at the second port 122 of the concentration unit 120, there is no reverse flow at the communication portion.

In the third embodiment, the purge step and the desorption step may occur simultaneously. For example, when the carrier gas flows through the concentration unit 120, a part of the carrier gas flowing from the communication portion to the dehydration unit 110 can take water or water vapor in the dehydration unit 110 away from the dehydration unit 110. Herein, it is necessary to heat both the dehydration unit 110 and the concentration unit 120. To achieve a compact design, in the third embodiment, only one heating apparatus is provided, which can heat both the dehydration unit 110 and the concentration unit 120, for example, to 250-350° C. At the raised temperature, the volatile organic compounds in the concentration unit 120 can be desorbed, and condensed substances (such as condensed water, ice, ice crystals, and an ice-water mixture) in the dehydration unit 110 can be converted into water vapor. Therefore, when flowing through the dehydration unit 110, the carrier gas may be used as a purge gas to blow away the water vapor, thus improving the overall efficiency. As mentioned above, due to the internal pressure, the water or water vapor in the dehydration unit 110 does not reversely flow into the concentration unit 120 through the communication portion.

It can be understood that in the sampling mode, the port of the concentration unit 120 in communication with the analysis unit 170 is closed. In addition, the first port 112 of the dehydration unit 110 and the second port 122 of the concentration unit 120 are located on the same side, rather than at two opposite ends as shown in the first and second embodiments.

In addition, in this third embodiment, it is also possible to use only one cooling apparatus 130 to cool the dehydration unit 110 and the concentration unit 120 together to achieve the goal of low temperature. For example, the cooling apparatus 130 may be arranged outside the dehydration unit 110 and the concentration unit 120, as shown in FIG. 3. Advantageously, in the sampling mode, there is no need to heat the concentration unit 120 by means of a separate heating apparatus. Specifically, the second tube as the concentration unit 120 is located inside the first tube as the dehydration unit 110, and there is a spatial gap between the second tube and the first tube. In this spatial gap, there is a heat insulating gas, such as the sample gas. Therefore, the temperature of the first tube is generally slightly less than that of the second tube, that is, the second preset temperature is slightly less than the first preset temperature, so as to ensure that no condensed substances or ice blockage is generated in the concentration unit 120.

In the three embodiments described above, the entire gas path from the dehydration unit 110 to the concentration unit 120 (optionally further including other gas paths for branch-off or for delivery into the analysis unit 170) has a very compact design. There is a relatively small distance between the dehydration unit 110 and the concentration unit 120, and the dehydration unit and the concentration unit may even be integrated into one tube. Moreover, at least some ports can achieve a plurality of different functions, thus achieving the purpose of multifunctional integration. It can be understood that the compact structure can further minimize the risk of air tightness failure between the dehydration unit 110 and the concentration unit 120 (mainly in the sampling mode) when there is a large temperature change.

Although various embodiments of the present invention are described in the accompanying drawings with reference to various examples of gas detection devices and gas detection methods for detecting volatile organic compounds in sample gases, it is understood that embodiments within the scope of the present invention may be applied to systems, devices, and methods of similar structure and/or function.

Many features and advantages have been given in the preceding descriptions, including various alternative embodiments, as well as details of the structure and function of the devices and methods. The intent herein is exemplary and not exhaustive or limiting.

It is apparent to those skilled in the art that various adaptations may be made to the full extent indicated by the broad superordinate meanings of the terms expressed in the appended claims, particularly with respect to structure, materials, elements, components, shapes, sizes, and arrangements of components, including combinations of these within the scope of the principles described herein. To the extent that these various modifications do not depart from the spirit and scope of the appended claims, it is implied that they are also encompassed herein.

The invention claimed is:

1. A gas detection device for detecting volatile organic compounds in a sample gas, comprising:
   a dehydration unit configured to dehydrate the sample gas flowing into the dehydration unit by condensation, the dehydration unit comprising a first port;
   a concentration unit arranged downstream of the dehydration unit in a flow direction of the sample gas and in fluid communication with the dehydration unit, the concentration unit comprising a second port; and
   a temperature control unit for controlling a temperature, wherein the gas detection device includes a sampling mode, in which the sample gas flows into the dehydration unit through the first port and flows out of the concentration unit through the second port, wherein the volatile organic compounds in the sample gas are concentrated in the concentration unit, and the temperature control unit is configured such that the temperature of the sample gas after flowing out from the dehydration unit and before flowing into the concentration unit is not greater than a first preset temperature set by the temperature control unit for the concentration unit, wherein the gas detection device further comprises an analysis unit for analyzing the volatile organic compounds, and includes a desorption mode, in which a carrier gas flows into the concentration unit from the second port, such that the volatile organic compounds desorbed from the concentration unit flows to the analysis unit with the carrier gas, wherein the dehydration unit comprises a reduced-diameter portion that has a reduced diameter in the flow direction of the sample gas, and in the sampling mode, the sample gas flows out of the dehydration unit through the reduced-diameter portion, and in the desorption mode, a part of the carrier gas can flow into the dehydration unit through the reduced-diameter portion for branch-off.

2. The gas detection device according to claim 1, wherein the temperature control unit comprises a cooling apparatus that can cool an entire sample gas flow path from the dehydration unit to the concentration unit.

3. The gas detection device according to claim 2, wherein the temperature control unit comprises a first heating apparatus for heating the dehydration unit and/or a second heating apparatus for heating the concentration unit.

4. The gas detection device according to claim 3 wherein the second heating apparatus comprises a heat generating mechanism arranged around the concentration unit and an insulating sleeve arranged outside of the heat generating mechanism and configured to fix the heat generating mechanism.

5. The gas detection device according to claim 1, wherein the temperature control unit is configured to make the first preset temperature greater than a second preset temperature set for the dehydration unit by a first temperature difference, wherein the first temperature difference is 0° C. to 10° C., and the second preset temperature is in a range of −45° C. to −35° C.

6. The gas detection device according to claim 1, wherein the gas detection device comprises a capillary tube which includes a first open end and a second open end, wherein the first open end is in communication with the analysis unit, and the second open end is in fluid communication with an interior of the concentration unit, and wherein in the desorption mode, the carrier gas loaded with the volatile organic compounds can flow to the analysis unit through the capillary tube.

7. The gas detection device according to claim 6, wherein the second open end is located inside the dehydration unit, such that in the desorption mode, the carrier gas containing the volatile organic compounds flows into the capillary tube inside the dehydration unit, wherein a part of the carrier gas can be branched off by means of at least one of the first port and another port of the dehydration unit.

8. The gas detection device according to claim 1, wherein the gas detection device further includes a purge mode, in which the temperature control unit can heat the dehydration unit to convert condensed substances therein into water vapor, such that the water vapor can be blown out from the dehydration unit.

9. A method for detecting volatile organic compounds in a sample gas by using a gas detection device, the gas detection device comprising a dehydration unit with a first port and a concentration unit with a second port, wherein the method comprises a sampling step, in which the sample gas flows into the dehydration unit through the first port and flows out of the concentration unit through the second port, wherein the sampling step comprises:

dehydrating the sample gas by condensation in the dehydration unit;

concentrating the volatile organic compounds in the sample gas within the concentration unit; and controlling a temperature of the sample gas, such that the temperature of the sample gas after flowing out from the dehydration unit and before flowing into the concentration unit is not greater than a first preset temperature set for the concentration unit, wherein the gas detection device further comprises an analysis unit for analyzing the volatile organic compounds, the method further comprises a desorption step performed after the sampling step, wherein said desorption step includes heating the concentration unit to desorb the volatile organic compounds, making a carrier gas flow through the concentration unit, to carry the desorbed volatile organic compounds out of the concentration unit and to the analysis unit, wherein the dehydration unit comprises a reduced-diameter portion that has a reduced diameter in the flow direction of the sample gas, and in the sampling step, the sample gas flows out of the dehydration unit through the reduced-diameter portion, and in the desorption step, a part of the carrier gas can flow into the dehydration unit through the reduced-diameter portion for branch-off.

10. The method according to claim 9, wherein the sampling step further comprises: controlling the temperature of the sample gas to make the first preset temperature greater than a second preset temperature set for the dehydration unit by a first temperature difference, wherein the first temperature difference is 0° C. to 10° C., and the second preset temperature is in a range of −45° C. to −35° C.

11. The method according to claim 10, wherein the method comprises a purge step performed after the sampling step, wherein the purge step comprises: heating the dehydration unit to convert condensed substances therein into water vapor, and blowing the water vapor out from the dehydration unit.

* * * * *